United States Patent
De Cock De Rameyen et al.

(10) Patent No.: US 12,007,600 B2
(45) Date of Patent: Jun. 11, 2024

(54) POLYMER OPTICAL FIBRE FOR ACTIVE IMPLANTABLE MEDICAL DEVICES (AIMD) AND AIMD USING SAME

(71) Applicant: Synergia Medical, Mont-Saint-Guibert (BE)

(72) Inventors: Aurélie De Cock De Rameyen, Mont-Saint-Guibert (BE); Pascal Doguet, Mont-Saint-Guibert (BE); Vincent Callegari, Mont-Saint-Guibert (BE); Aurore Nieuwenhuys, Mont-Saint-Guibert (BE)

(73) Assignee: Synergia Medical, Mont-Saint-Guibert (BE)

( * ) Notice: Subject to any disclaimer, the term of this patent is extended or adjusted under 35 U.S.C. 154(b) by 293 days.

(21) Appl. No.: 17/635,062

(22) PCT Filed: Aug. 14, 2019

(86) PCT No.: PCT/EP2019/071803
§ 371 (c)(1),
(2) Date: Feb. 14, 2022

(87) PCT Pub. No.: WO2021/028034
PCT Pub. Date: Feb. 18, 2021

(65) Prior Publication Data
US 2022/0291442 A1    Sep. 15, 2022

(51) Int. Cl.
*G02B 6/02*    (2006.01)
*C08L 23/08*    (2006.01)
(Continued)

(52) U.S. Cl.
CPC ...... *G02B 6/02033* (2013.01); *C08L 23/0823* (2013.01); *C08L 27/14* (2013.01);
(Continued)

(58) Field of Classification Search
CPC ................. G02B 6/02033; B29D 11/00063
See application file for complete search history.

(56) References Cited

U.S. PATENT DOCUMENTS

| 5,148,511 A | 9/1992 | Savu et al. |
| 9,103,966 B2 | 8/2015 | Lin et al. |
| | (Continued) | |

FOREIGN PATENT DOCUMENTS

| EP | 2513680 A1 | 10/2012 |
| JP | 2000-275448 A | * 10/2000 |
| | (Continued) | |

OTHER PUBLICATIONS

F. Reifler et al. Polymer optical fibers for textile applications—Bicomponent melt spinning from cyclic olefin polymer and structural characteristics revealed by wide angle X-ray diffraction. Polymer, 55:22:5695-5707, Oct. 2014. (https://doi.org/10.1016/j.polymer.2014.08.071) (Year: 2014).*

(Continued)

*Primary Examiner* — Michael Stahl
(74) *Attorney, Agent, or Firm* — MaxGoLaw PLLC

(57) ABSTRACT

A polymer optical fibre (POF) (30) for transmitting light of wavelength, λi, between two separate elements of an active implantable medical device (AIMD), includes a core (31) which is cylindrical and made of a cyclic olefin polymer (COP) or copolymer (COC), having a core refractive index at the wavelength, λi, n_core, A cladding (32) which has a cladding refractive index at the wavelength, λi, n_clad<n_core, and which is made of a cladding copolymer including monomers of tetrafluoroethylene, hexafluoropropylene and vinylidene fluoride. The cladding being itself enclosed in a coating (33) which is made of a coating polymer formed of one of the monomers of the cladding (Continued)

copolymer. The POF has a numerical aperture, NA, at the wavelength, $\lambda i$, of at least 0.5.

19 Claims, 5 Drawing Sheets

(51) Int. Cl.
    *C08L 27/14*     (2006.01)
    *C08L 27/18*     (2006.01)
    *C08L 27/20*     (2006.01)
    *G02B 1/04*     (2006.01)

(52) U.S. Cl.
    CPC .............. *C08L 27/18* (2013.01); *C08L 27/20* (2013.01); *G02B 1/046* (2013.01); *G02B 1/048* (2013.01); *G02B 6/02047* (2013.01); *C08L 2203/02* (2013.01); *C08L 2203/202* (2013.01)

(56) References Cited

U.S. PATENT DOCUMENTS

| | | |
|---|---|---|
| 2009/0279837 A1* | 11/2009 | Aoyagi .................. G02B 1/045 |
| | | 385/100 |
| 2011/0125078 A1 | 5/2011 | Denison et al. |
| 2011/0245714 A1 | 10/2011 | Volckaerts |
| 2014/0155948 A1 | 6/2014 | Walsh et al. |
| 2016/0015467 A1 | 1/2016 | Vayser et al. |
| 2020/0301064 A1 | 9/2020 | Kojima et al. |

FOREIGN PATENT DOCUMENTS

| | | | |
|---|---|---|---|
| JP | 2022-113969 A | * | 8/2022 |
| WO | 2019059160 A1 | | 3/2019 |

OTHER PUBLICATIONS

Int'l Search Report for PCT/EP2019/071803, dated May 11, 2020.

* cited by examiner

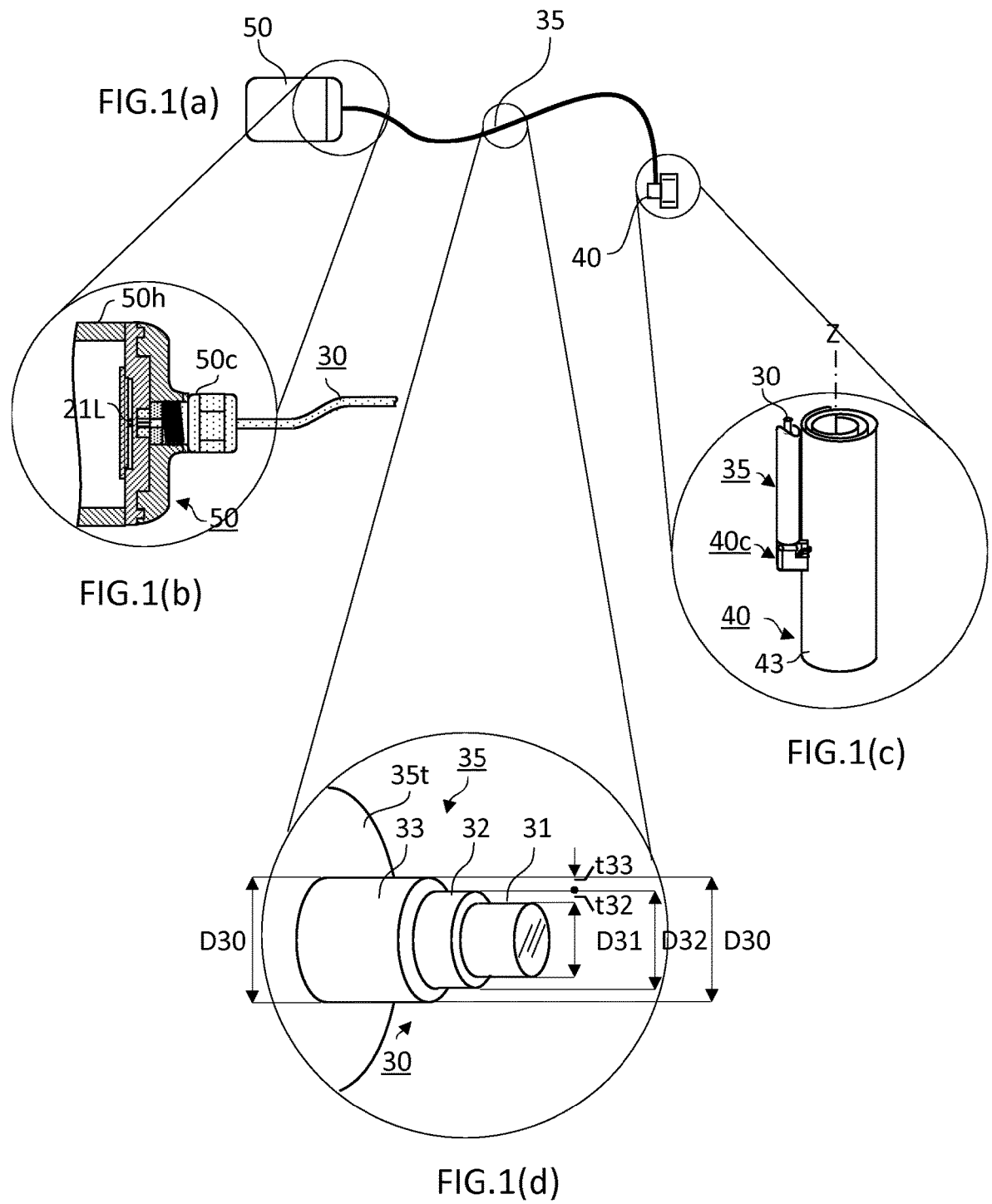

$$NA = \sqrt{n_{core}^2 - n_{clad}^2} \qquad \theta_c = asin\frac{n_{clad}}{n_{core}}$$

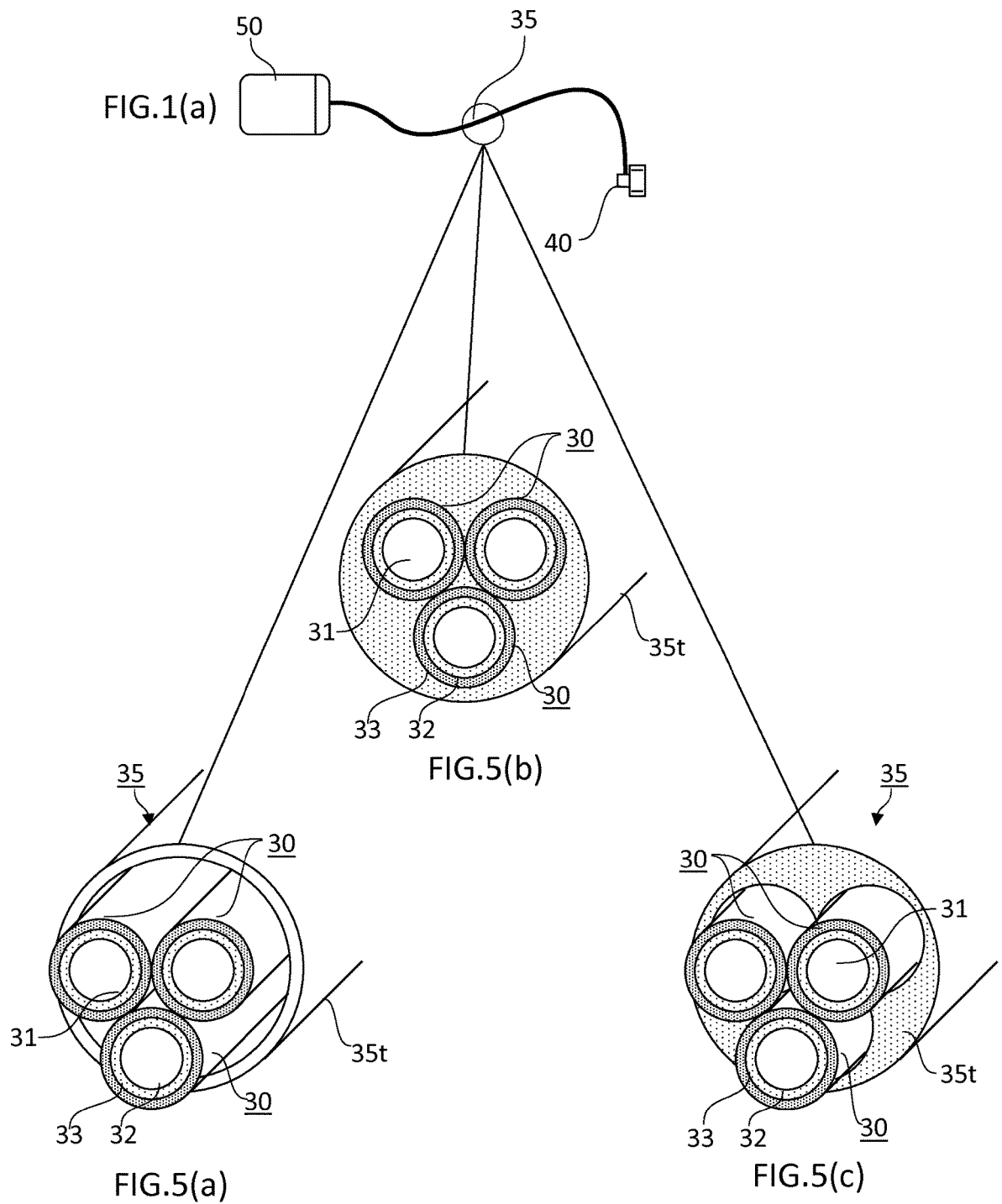

POLYMER OPTICAL FIBRE FOR ACTIVE IMPLANTABLE MEDICAL DEVICES (AIMD) AND AIMD USING SAME

TECHNICAL FIELD

The present invention is in the field of optoelectronic active implantable medical devices (AIMD) for use in medical treatments involving the transmission of energy pulses between a light pulse generator enclosed in an encapsulation unit and a biological tissue by transmission of optical energy through optical fibres between the encapsulation unit and the biological tissue. In particular, it concerns a novel polymer optical fibre combining all the requirements for use in an implanted AIMD, including high numerical aperture (NA), high flexibility, high biocompatibility, high hydrophobicity, high dimensional, mechanical, and chemical stability, easy polishing, and low values of bending radius, low outer diameter, and low optical losses. Most importantly, compared with optical fibres having a glass core which are brittle, the polymer optical fibre of the present invention is very safe for implantation in a human or animal body.

BACKGROUND OF THE INVENTION

Active implantable medical devices (AIMD) have been used for decades for treating a number of disorders, in particular neurological disorders. A major type of AIMD's consists of neurostimulators, which deliver electrical pulses to a tissue such as a nerve or a muscle for diagnosing or treating a number of disorders such as Parkinson's disease, epilepsy, chronic pain, motor disorders, and many other applications. Depending on the tissue to be treated, the type of electrodes used, and the distance between electrodes, the voltage required between implanted electrodes is generally of the order of 15V±5V. Such voltage requires an electrical pulse generator of such dimensions that electric stimulating implants are generally formed of two separate components: on the one hand, the electrodes which are implanted directly onto the tissue to be treated and, on the other hand, the electrical pulse generator, of larger dimensions, and encapsulated in a housing, which can be implanted at various locations in the body depending upon the application but most often in the subclavian region, the lower abdominal area or gluteal region. The wires connecting the pulses generator to the electrodes are generally coiled to provide flexibility, to permit the distance from the electrical pulse generator and the electrodes to be varied and to enhance mechanical stability with a higher compliance with respect to body movements. Because of the use of electric wires, in particular when coiled, such implants are not recommended for exposure to magnetic resonance imaging (MRI) apparatuses and also to simple metal detecting portals as used in airports, banks, and the like.

In its simplest form, a device for delivering electrical pulses comprises an energy pulse generator lodged in a housing, stimulating electrode contacts, and leads coupling the electrode contacts to the energy pulse generator to transmit energy from the energy pulse generator to the electrode in the form of electrical energy. The energy pulse generator can generate electrical pulses transmitted to the electrode contacts by conductive leads. Alternatively, and as described, e.g., in EP3113838B1, the energy pulse generator can generate light pulses transmitted through optical fibres to photovoltaic cells which transform the light energy into electrical energy which is fed to the electrode contacts.

In recent years, treatment of tissues with optical energy has shown encouraging potential for the treatment of disorders, either to support the field of optogenetics or using direct infrared light. For such light treatments of a tissue, a so-called optrode can be used. An optrode can be a light emitter focusing a light beam onto a precise area of a tissue, or it can be a light sensor, sensing a reflected, transmitted, or scattered light beam emitted by a light emitter.

As illustrated in FIG. 1, the polymer optical fibres (POF) of the present invention are for use with an optoelectronic AIMD which comprises:
- an encapsulation unit (50) including a housing enclosing a source of energy, any analogue and/or digital circuit, such as a pulse generator, and a source of light emission (21L) and/or a light sensor,
- a tissue coupling unit (40) comprising one or more electrodes and/or optrodes suitable for being implanted directly onto a tissue to be treated, and
- an optical lead (35) comprising one or more polymer optical fibres (30) (POF) for transferring optical energy between the encapsulation unit and the tissue coupling unit.

In continuation such AIMD's are referred to as "optoelectronic AIMD's" and polymer optical fibres are referred to as "POF."

The implantation of an optoelectronic AIMD includes the following steps. A surgeon opens the area comprising the tissue to be treated and couples the tissue coupling unit to said tissue. The tissue coupling unit is often optically coupled to the distal ends of one or more POF's before implanting the tissue coupling unit to the tissue to be treated. Coupling of optical fibres to an electrode unit is described e.g., in PCT/EP2017/071858.

Proximal ends of the one or more optical fibres (opposite the distal end) are then subcutaneously led through a specific guide to the area of implantation of the encapsulation unit, which is dimensionally substantially larger than the electrode unit and is therefore implanted in more appropriate parts of the body. The surgeon can implant the encapsulation unit and couple it to the proximal ends of the optical fibres (in any sequence).

As shown in FIG. 2(a), optical fibres are fine composite glass or plastic fibres which allow transportation of light from one end to the opposite end of the optical fibre. An optical fibre comprises a core (31) surrounded by a cladding (32) which are normally made of silica glass or plastic. The optical fibre transmits an optical beam along the core, the optical beam being reflected internally whenever reaching a core-cladding interface with an angle smaller than a critical angle θc. Optical beams can thus be guided even along curvilinear paths.

As illustrated in FIG. 2(b), multi-mode optical fibres only propagate light entering the fibre with an incident angle smaller than an acceptance angle, Amax, defining an acceptance cone of the fibre, which half-angle of this cone is called the acceptance angle, θmax. The critical angle, θc, defined as, $\sin\theta c = n_{clad}/n_{core}$, is the angle of incidence in the core at the core-cladding interface, for which angle of refraction become 90°. The numerical aperture, NA, of an optical fibre defines a light gathering capacity of an optical fibre. The numerical aperture is defined as, $NA = n0 \sin\theta max = \sqrt{n_{core}^2 - n_{clad}^2}$, wherein n0, n_core and n_clad are the refractive indices of the medium around the fibre, the core, and the cladding, respectively.

Optical fibres have been mainly used for data transfer over long distances and at high bandwidths with optical fibres including a core generally made of glass. Polymer optical fibres (POF) have been proposed to replace glass made optical fibres. Most of the glass made optical fibres (GOF's) have a core made of fused silica and, as shown in FIG. 3, yield higher optical transmission in the near infrared (700-2000 nm) than POF's. GOF's, however, are brittle which is unacceptable for safety reasons in applications including an AIMD implanted in a patient's body. Furthermore, because of glass brittleness, GOF's have a very limited bending radius, R, which is defined as the lowest inner radius an optical fibre can be bent to without damaging it and while still acting as waveguide (cf. FIG. 2(c)). Consequently, in spite of their excellent optical properties GOF's are ill suited for use in AIMD's. POF's are herein defined as optical fibres with at least the core made of polymer and GOF's are defined as optical fibres with at least the core made of glass (generally fused silica).

As can be seen in FIG. 3, showing the attenuation per unit length of optical fibres for GOF and for various POF's, POF's suffer optical attenuation which is three orders of magnitude higher than GOF's in the wavelength range of 700 to 900 nm. These values are, however, still acceptable because the length of an optical fibre in an AIMD is only of the order of 30 to 50 cm, preferably between 35 and 45 cm.

In spite of their lower transmission (i.e., higher attenuation, as shown in FIG. 3) compared with GOF's, POF's have drawn much attention because of their higher flexibility and lower to no brittleness, the latter being a sine qua non condition for use in an AIMD implanted in a patient's body. Polymers such as polymethyl methacrylate (PMMA), polycarbonate (PC), polystyrene (PS), or cyclic polyolefin polymers or copolymers (COP, COC) have been used for the core, with different claddings, including silicone, fluoropolymers, PMMA. PMMA has been proposed for use in house or automotive wiring in U.S. Pat. No. 5,148,511 with a fluoropolymer cladding. A POF of similar composition was described in US2012020637. PMMA, however, has a major drawback in that upon exposure to moisture, it swells with a corresponding variation of the refractive index and it becomes brittle and forms cracks. Since a POF implanted in a patient's body is exposed to high moisture levels, it is not an acceptable candidate to replace GOF's.

Various applications have been described using cyclic olefin polymers or copolymers (COP, COC) as core material with various fluoropolymers as cladding materials, such as in US20160015467 in the field of surgical instruments. COP's and COC's chemical structures are illustrated in FIG. 4(a).

COP's and COC's are hydrophobic, are available as biocompatible materials. They are very stable to moisture and, together with fluoropolymers as cladding materials have values of NA higher than 0.7. These types of POF's seemed promising for use in AIMD's applications.

Upon testing POF's comprising a core made of COP with a fluoropolymer cladding, a problem arose when polishing the free ends of the POF: the free ends were frayed, which is unacceptable in terms of transmission losses A polished cross-sectional surface of the ends of the POF's is essential to reduce transmission losses at the level of the connections between the POF and any other device, such as another optical fibre, the encapsulation or the tissue coupling unit. Because the implanted AIMD is powered by a battery generally stored in the encapsulation, energy losses must be avoided in order to prolong the autonomy of the battery. For rechargeable batteries, it is advantageous to extend the period between two successive charging operations, which are demanding operations for the patient and affect the service life of the batteries. A POF which ends cannot be polished properly are ill-fitted for use in implanted AIMD's The present invention proposes a POF which combines easy mechanical polishing of the free ends to yield a smooth surface finish of the free ends (thus reducing the transmission losses at connection points) with biocompatibility and hydrophobicity of the materials used. With an acceptable attenuation typical of current POF's, the POF of the present invention is suitable for implanted AIMD's applications, as it combines high safety with a high flexibility, and low bending radii. These and other advantages are described in more details in the following sections.

SUMMARY OF THE INVENTION

The present invention is defined in the appended independent claims. Preferred embodiments are defined in the dependent claims. In particular, the present invention concerns a polymer optical fibre (POF) for transmitting light of wavelength, $\lambda i$, between two separate elements of an active implantable medical device (AIMD), wherein the wavelength, $\lambda i$, is comprised between 380 and 1800 nm, preferably between 650 and 1550 nm, and wherein said POF is a multimode optical fibre comprising a first end and a second end, and comprising:
  (a) a core which is cylindrical and made of a cyclic olefin polymer (COP) or copolymer (COC), having a core refractive index at the wavelength, $\lambda i$, n_core, which is enclosed in
  (b) a cladding which has a cladding refractive index at the wavelength, $\lambda i$, n_clad<n_core, and which is made of a cladding copolymer comprising monomers of tetrafluoroethylene, hexafluoropropylene and vinylidene fluoride, the cladding being itself enclosed in
  (c) a coating which is made of a coating polymer comprising one of the monomers of the cladding copolymer, selected among monomers of tetrafluoroethylene, hexafluoropropylene and vinylidene fluoride wherein the POF has a numerical aperture, NA, at the wavelength, $\lambda i$, of at least 0.5, preferably at least 0.6, more preferably at least 0.7, wherein $NA=((n\_core)^2-(n\_clad)^2)^{1/2}$.

The cladding polymer can be a terpolymer of tetrafluoroethylene, hexafluoropropylene and vinylidene fluoride (THV). The coating polymer can be vinylidene fluoride (PVDF).

It is preferred that the first end and/or the second end of the polymer optical fibre is polished, preferably mechanically, chemically, mechanically-chemically polished, to maximize transmission of optical energy from and to the optical fibre. The first end and/or the second end are preferably mechanically polished The polymer optical fibre can have a diameter (D30) comprised between 150 and 530 μm, preferably between 250 and 480 μm. A diameter (D31) of the core can be comprised between 100 and 300 μm, preferably between 200 and 250 μm, more preferably between 220 and 240 μm. The cladding can have a thickness (t32) comprised between 5 and 50 μm, preferably between 7 and 25 μm, more preferably between 10 and 15 μm, or can have an outer diameter (D32) comprised between 130 and 500 μm, preferably between 110 and 400 μm. The coating can have a thickness (t33) comprised between 10 and 40 μm, preferably between 15 and 30 μm, more preferably between 20 and 25 μm.

The core polymer preferably has an attenuation lower than 4.0 dB/m, more preferably lower than 3.6 dB/m, at least at one wavelength comprised within the wavelength range from 550 nm to 875 nm. The optical loss relative to a straight fibre is preferably less than 2% at a bend radius of 2 mm.

The present invention also concerns an optical lead for transmitting light of wavelength, $\lambda i$, between two separate elements of an active implantable medical device (AIMD), comprising one or more than one polymer optical fibres as described supra enclosed in an outer tubing.

At least one polymer optical fibre of the optical lead can be coloured. For example said at least one polymer optical fibre can comprise a coloured coating or a coloured cladding combined with a transparent coating. In one embodiment the optical lead is visible to X-rays. This can be achieved by including an X-ray visible additive such as $BaSO_4$, to the outer tubing or to the coatings (33) of one or more of the polymer optical fibres of the optical lead.

The present invention also concerns an active implantable medical device (AIMD) comprising,
(a) an encapsulation comprising a source of light emitting at least at a wavelength, $\lambda I$, comprised between 380 and 1800 nm, preferably between 600 and 1500 nm,
(b) a tissue coupling unit, separate from the encapsulation and comprising a photovoltaic cell and/or a photosensor, and/or an optrode,
(c) the source of light of the encapsulation being optically coupled to the first end of a polymer optical fibre as discussed supra, and the photovoltaic cell and/or photosensor and/or optrode of the tissue coupling unit being optically coupled to the second end of the polymer optical fibre, such that the source of light is in optical communication with the photovoltaic cell and/or photosensor and/or optrode through the polymer optical fibre.

The AIMD preferably comprises more than one polymer optical fibres gathered in an outer tubing to form an optical lead as discussed supra.

In a preferred embodiment, the second component is a cuff electrode unit comprising a photovoltaic cell, and comprising,
a support sheet which is non-conductive, and having an inner surface and an outer surface separated from the inner surface by a thickness, wherein the support sheet is rolled about a longitudinal axis (Z), forming a cuff of substantially cylindrical geometry such that at least a portion of the inner surface forms an interior of the cuff, and such that at least a portion of the outer surface forms an exterior of the cuff,
at least a first connector including an electrode contact, which is exposed at the inner surface of the cuff and wherein
the photovoltaic cell is optically coupled to the second end of the polymer optical fibre and therethrough to the source of light emission (21L) and is electrically coupled to the electrode contact.

BRIEF DESCRIPTION OF THE FIGURES

For a fuller understanding of the nature of the present invention, reference is made to the following detailed description taken in conjunction with the accompanying drawings in which:
FIG. 1: shows (a) an AIMD according to the present invention, comprising (b) an encapsulation unit, (c) a tissue coupling unit, and (d) an optical lead comprising a POF according to the present invention.
FIG. 5: shows three examples of optical leads comprising three POF's according to the present invention enclosed in (a) a sheath, (b) embedded in an outer coating, and (c) inserted in mating elongated orifices of a rod.

DETAILED DESCRIPTION OF THE INVENTION

As illustrated in FIG. 1(d), a polymer optical fibre (POF) (30) according to the present invention comprises a core (31) surrounded by a cladding (32) and itself surrounded by a coating (33). The POF is a multimode optical fibre comprising a first end and a second end and is designed for transmitting light of wavelength, $\lambda i$, between two separate elements of an active implantable medical device (AIMD), wherein the wavelength, $\lambda i$, is comprised between 380 and 1800 nm, preferably between 650 and 1550 nm, more preferably between 700 and 900 nm.

Core (31)

Figure 4A:
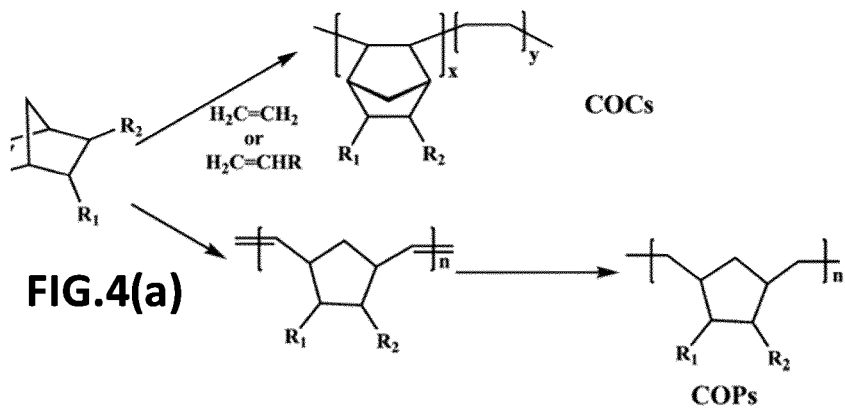
FIG. 4: shows the chemical structures of (a) COP and COC of the core, (b) THV of the cladding, and (c) PVDF, PTFE, and PHFP of the coating.

The core (31) is generally cylindrical and is made of a cyclic olefin polymer (COP) or copolymer (COC) which chemical structures are illustrated in FIG. 4(a). An example of COP is Zeonex, e.g., Zeonex 480 R available from ZEON CORPORATION, and an example of COC is TOPAS, e.g., TOPAS 5013 or TOPAS 8007 available from TOPAS Advanced Polymers, Inc.

The core (31) has a core refractive index, n_core, at the wavelength, $\lambda i$. Cyclo olefin polymer/copolymer (COP, COC) is hydrophobic and has <0.01% water absorption which is substantially lower than PC or PMMA. COP's and COC's are dimensionally stable and the optical properties remain substantially stable upon exposure to various humidity environments. For example, Zeonex has a refractive index, n_core, varying from 1.509 to 1.535 depending on the grades, with n_core=1.531 at a wavelength of 486 nm for Zeonex E48 R, which remains stable for at least 14 days at 50° C. in an atmosphere of 90% RH. In comparison, the refractive index, n_core, of PMMA in the same test conditions varied from 1.490 to 1.492 due to moisture absorption.

The core (31) of the POF preferably has a diameter (D31) comprised between 100 and 300 μm, more preferably between 200 and 250 μm, most preferably between 220 and 240 μm. COP's and COC's can be drawn to such filament diameters with no particular problem.

With a flexural modulus of the order of 2.1 GPa, cyclo-olefin polymer/copolymer (COP, COC) fibres are very flexible, even more than corresponding PMMA or PS fibres, with flexural moduli of the order of 3.0 GPa. Optical fibres comprising a COP or COC core can therefore be bent sharply without breaking, ensuring safety for long term implantations without any risk of brittle fracture. This requirement is essential for use of an optical fibre in an AIMD.

Figure 3:
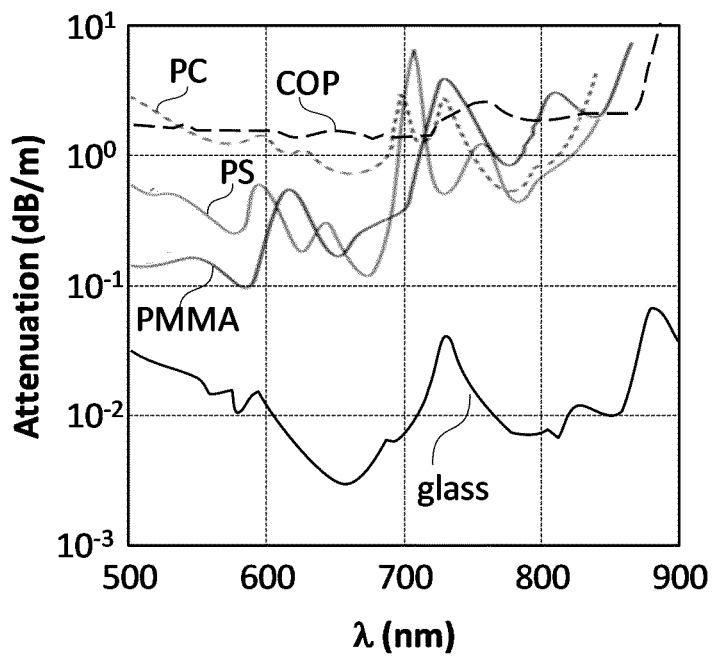
FIG. 3: shows the attenuation of various POF's compared with a GOF.

The core polymer has an attenuation preferably lower than 4.0 dB/m, preferably lower than 3.6 dB/m, at least at one wavelength comprised within the wavelength range from 550 nm to 875 nm. COP's and COC's have an optical attenuation of the order of 2 to 3 dB/m (=2 to 3 $10^3$ dB/km) in the wavelength range from 550 nm to 875 nm (cf. FIG. 3).

Cladding (32)

Figure 2A:
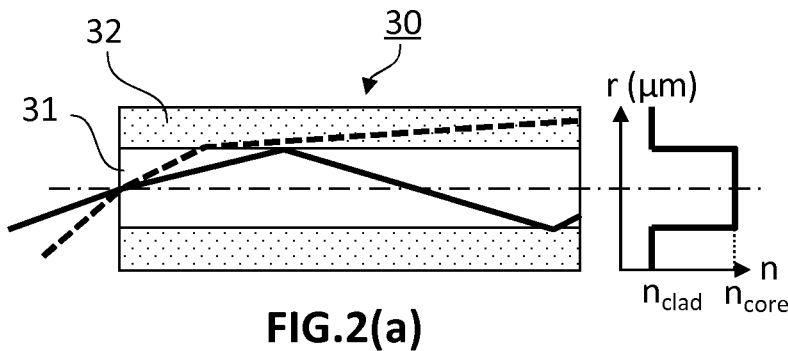
FIG. 2: shows an optical fibre showing (a) principle of waveguide of a light beam by internal reflection at the core-cladding interface, (b) the numerical aperture (NA) and critical angle ($\theta c$), (c) bending angle and effect on the propagation of a light beam, and (d) plot of the critical angle as a function of NA, for a core having n_core=1.531.

As explained supra, an optical fibre requires a core and a cladding to transport light from one end to the other of the optical fibre. The cladding (32) has a cladding refractive index at the wavelength, λi, n_clad<n_core, to allow reflection of a light beam reaching the core-cladding interface (cf. FIG. 2(a)).

Figure 4B:
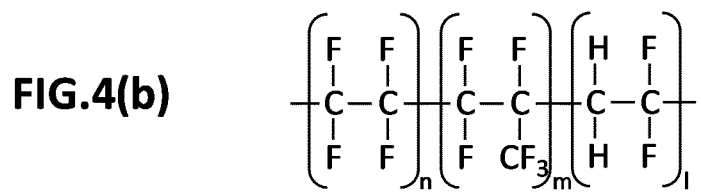

The cladding of the present invention is made of a cladding copolymer comprising monomers of tetrafluoroethylene, hexafluoropropylene and vinylidene fluoride. The cladding copolymer can be a terpolymer of tetrafluoroethylene, hexafluoropropylene and vinylidene fluoride (THV), of chemical structure as illustrated in FIG. 4(b).

It is preferred that the COP/COC core and the cladding materials be selected such as to yield a numerical aperture, NA=$\sqrt{n_{core}^2 - n_{clad}^2}$, at the wavelength, λi, of at least 0.5, preferably at least 0.6, more preferably at least 0.7. For example, if the core is made of Zeonex E48R having a refractive index, n_core=1.531, a POF having a NA>0.7 is obtained with a cladding material having a refractive index, n_clad≤1.36.

Examples of suitable cladding materials include THV200, THV220, THV415, THV500, THV X610, and THV815. They have relatively low processing temperatures and are very flexible, which is very useful for decreasing the bending radius, R, of the POF. The refractive index of THV's varies between 1.353 and 1.363, depending on the grade. For example, THV500 has a refractive index, n_clad=1.355. A POF comprising a core made of Zeonex E48R with n_core=1.531 and a cladding made of THV500 with n_clad=1.355 yields a numerical aperture, NA=0.713. The corresponding critical angle of reflection, $\theta_c$=a sin ($n_{clad}/n_{core}$)=53 deg (cf. FIG. 2(d)).

Figure 6A:
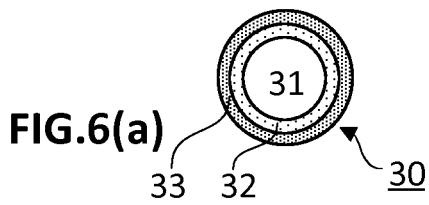
FIG. 6: shows various embodiments of POF's, comprising, (a) a single core in a cladding and coating, (b) several core-cladding units embedded in a single coating, (c) several cores embedded in a single cladding and a single coating, and (d) several multicore-cladding units enclosed in a single coating, wherein each multicore-cladding unit comprises several cores in a single cladding.
Figure 6B:
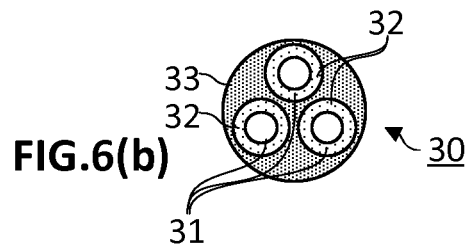
Figure 6C:
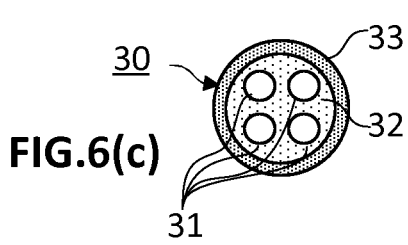
Figure 6D:
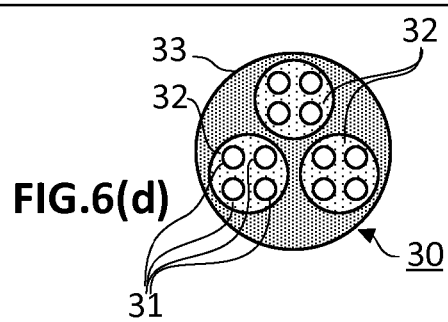
Figure 7A:
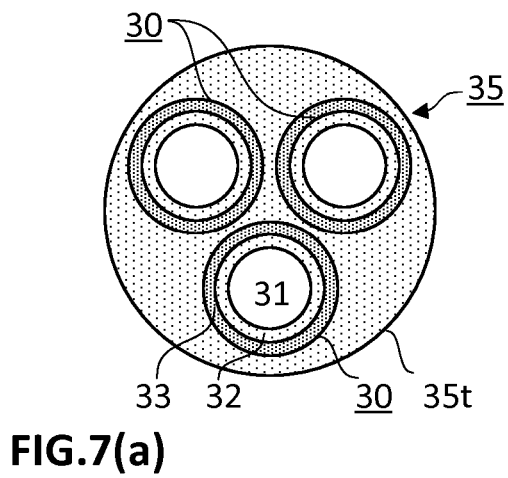
FIG. 7: shows various embodiments of optical leads comprising several POF's according to the embodiments (a) to (d) of FIG. 6 enclosed in an outer tubing.
Figure 7B:
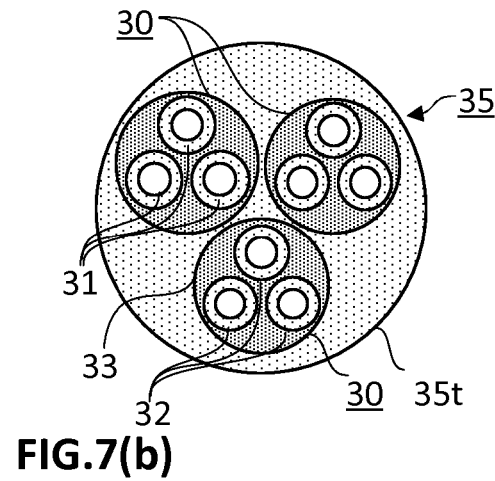
Figure 7C:
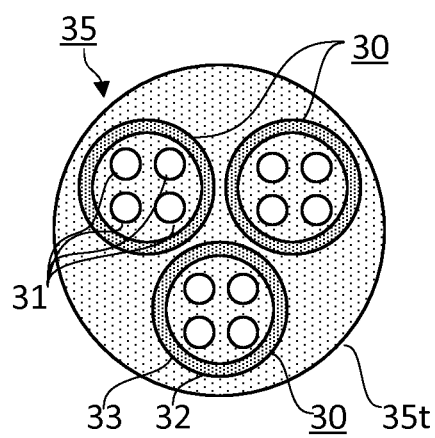
Figure 7D:
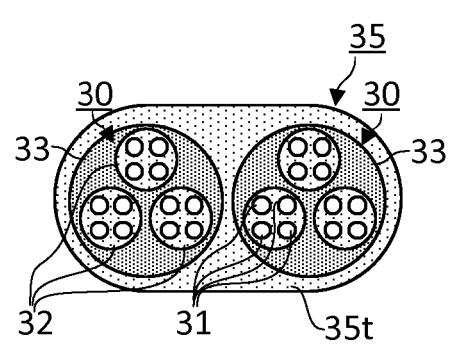

In one embodiment, a single core (31) is embedded in a cladding, as illustrated in FIGS. 1(d) and 6(a). In this embodiment, the cladding is preferably, albeit not necessarily, cylindrical. Alternatively, more than one core (31) can be enclosed in a single cladding, as illustrated in FIGS. 6(c) & 6(d).

The cladding can have an outer diameter (D32) comprised between 130 and 500 μm, preferably between 110 and 400 μm. If the cladding (32) embeds a single core (31) (cf. FIGS. 1(d) and 6(a)), it can have a thickness (t32) comprised between 5 and 50 μm, preferably between 7 and 25 μm, more preferably between 10 and 15 μm. For non-cylindrical claddings, the values of the hydraulic diameter have to be considered instead, wherein the hydraulic diameter is defined as Dh=4 A/P, wherein A and P are the area and perimeter of the cross-section of the core(s)-cladding unit.

A POF made of a core (31) and a cladding (32) as described above, fulfil many of the criteria for being suitable as a POF for use with an implanted AIMD. It is hydrophobic, resistant to moisture, has excellent flexibility and good optical properties, and biocompatible grades of all materials are available off the shelves. Because an AIMD is self-powered, with a (rechargeable) battery enclosed in the encapsulation, all sources of optical losses must be minimized, viz., losses due to attenuation, bending, and coupling including polishing. The following points are potential sources of optical losses, which need be minimized.

Attenuation losses—this has been discussed supra and, with an attenuation of 2 to 3 dB/m over a POF length of about 0.4 m, attenuation is of the order of 0.8 to 1.2 dB, which is acceptable and typical of POF's.

Figure 2B:
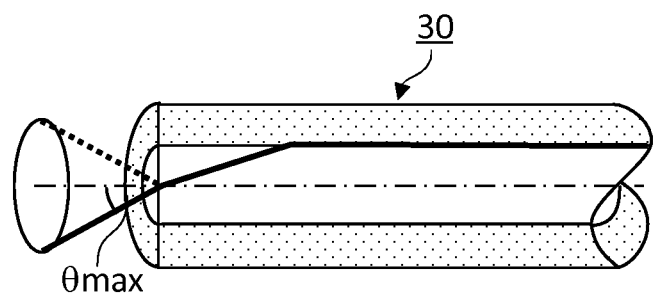
Figure 2C:
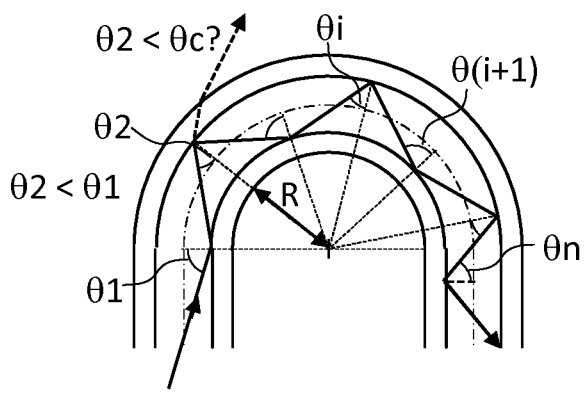
Figure 2D:
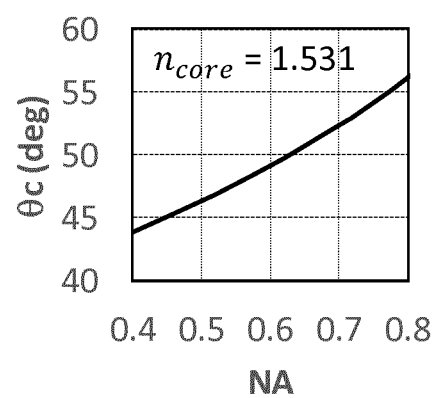

Bending losses—As illustrated in FIG. 2(c), an optical fibre can be bent. One major advantage of POF's over GOF's is their higher flexibility allowing lower bending radii to be reached mechanically. Mechanical flexibility, however, is merely a necessary but non-sufficient condition for bending an optical fibre. Indeed, the angle of a light beam reaching the core-cladding interface in a bent section can become lower than in a straight section (cf. FIG. 2(c)). If the angle becomes smaller than the critical angle, θc, the optical fibre cannot act as a waveguide anymore and the light beam can be refracted through the cladding (cf. dashed arrow at "θ2<θc?" in FIG. 2(c)). Since, as illustrated in FIG. 2(d), the critical angle, θc, increases with the value of NA, bending losses are related to the NA of the fibre. The high NA of the core-cladding discussed supra yields low bending losses of optical power and full advantage of the (mechanical) flexibility of the POF's can be taken advantage of.

Coupling losses—This loss can be minimized by using specific optical fibres connectors, such as described in PCT/EP2018/073436. For a given connector, this loss is governed by the core diameter and the numerical aperture (NA) of the POF. High values of both core diameter and POF's AN-value matching the diameter and divergence of the laser source decreases the losses dues to coupling. With NA values generally greater than 0.7, the combination COP-core with a THV-cladding yields acceptable coupling losses.

Polishing losses—The sections of the POF's ends must be well polished in order to reduce the coupling power loss.

Whilst the levels of optical power losses due to attenuation, coupling, and bending are agreeable for AIMD's applications, it was not possible to polish the ends of the core-cladding units discussed supra without fraying the cross-sectional surfaces, the cladding delaminating from the core. This resulted in levels of polishing losses unacceptable for AIMD's applications.

Coating (33)

Figure 4C:
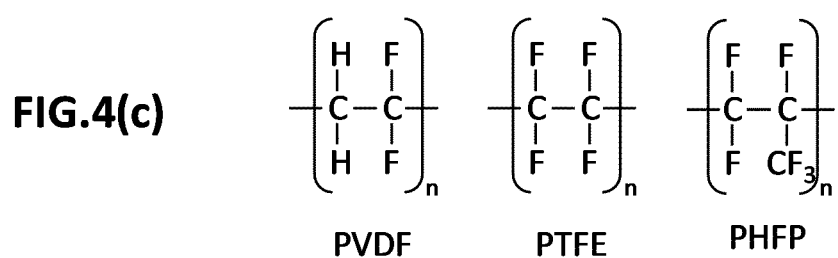

In order to enhance the polishing of the cross-sectional surfaces of the POF's ends, the POF of the present invention further comprises a coating (33) made of a coating polymer comprising one of the monomers of the cladding copolymer, selected among monomers of tetrafluoroethylene (PTFE), hexafluoropropylene (PHFP) and vinylidene fluoride (PVDF) which chemical structures are illustrated in FIG. 4(c). Preferably, the coating polymer is polyvinylidene fluoride (PVDF). The coating of the present invention is hydrophobic and absorbs substantially no moisture.

The coating defines the outer layer of the POF and has a diameter (D30) which can be comprised between 150 and 530 μm, preferably between 250 and 480 μm. If the coating (33) is not cylindrical, these values apply to the hydraulic diameter thereof. In case the coating (33) encloses a single cladding (32) (cf. FIG. 6(a)&6(c)), the coating can have a thickness (t33) comprised between 10 and 40 µm, preferably between 15 and 30 µm, more preferably between 20 and 25 µm.

By applying a coating polymer as defined supra, the cross-sectional surfaces of the ends of the POF can be mechanically polished to high surface finish without any fraying. Without wishing to be bound by any theory, it is believed that polishing is enhanced by the use of a coating if the following two conditions are fulfilled:
(a) the coating polymer has a higher stiffness than the cladding copolymer, and
(b) the coating polymer adheres to the cladding copolymer.

The coating (33) stabilizes the cladding (32), on the one hand, by its higher stiffness, thus restraining the movements of the cladding relative to the core, which adheres poorly thereto and, on the other hand, with its good adhesion to the cladding (32), the coating eliminates any movement of the cladding relative to the coating. For example, THV500 of the cladding (32) has a tensile modulus of about 200 MPa, and PVDF of the coating (33) has a tensile modulus of 1340 to 2000 MPa (PTFE has a tensile modulus of 400 to 800 MPa). The coating (33) of the present invention therefore fulfils the first condition (a)

Finding a polymer adhering to the fluoro-copolymer of the cladding is a challenge, because fluoropolymers have very low surface energies and are therefore difficult to adhere to. By selecting as coating material, a polymer comprising one of the monomers of the cladding copolymer, selected among monomers of tetrafluoroethylene, hexafluoropropylene and vinylidene fluoride, adhesion between cladding and coating is optimized, since similar chemical structures face each other across the interface. Tests have been performed with a POF comprising a COP-core, a THV500-cladding, and a COP-coating, and the polishing results were not satisfactory, although COP's have a tensile modulus of 2100 to 2740 MPa depending on the grades, which is higher than PVDF's. This failure is ascribed to a poor adhesion of COP to THV500, such that the second condition (b) is not fulfilled. By replacing the COP-coating by a PVDF coating, polishing ran smoothly and an optimal surface finish was obtained at the ends of the POF.

Furthermore, the first and second ends of the POF must be durably and reliably coupled to the encapsulation, e.g., facing a light source, and to the tissue coupling unit, e.g., facing a PV cell. To ensure that the optical fibre remains in perfect alignment with the corresponding optical elements, the first and second ends of the POF are inserted into corresponding cavities and glued in place with an adhesive. The cladding must therefore allow a good adhesion to the walls of the corresponding cavities, which can be made of a ceramic material, such as fused silica. The first and/or second ends of a POF can be glued to a cavity integral with the corresponding encapsulation and/or tissue coupling unit or, alternatively, to a cavity formed in a plug mating a socket integral with the corresponding encapsulation and/or tissue coupling unit. In an embodiment, the second end of a POF is glued directly to the tissue coupling unit, and the first end is glued to a plug mating a socket of the encapsulation. With this embodiment, a surgeon implants the tissue coupling unit provided with a POF to the corresponding tissue or nerve, drives subcutaneously the first end of the POF provided with the plug to the position of implantation of the encapsulation, and couples the plug to the socket of the encapsulation prior or after implanting the encapsulation. An example of plug suitable for use in an AIMD according to the present invention is described in PCT/EP2018073436.

Though a fluorinated component, PVDF yields acceptable adhesion to cavity walls made of fused silica when using an epoxy or a silicon resin as adhesive. Adhesion can be further enhanced by a surface treatment of the coating surface, such as a plasma or a corona treatment, prior to applying the adhesive to the treated surface. It is preferred that the refractive index of the adhesive be as close as possible, preferably equal to the one of the core of the POF, such that the cavity can first be filled with adhesive followed by inserting an end of the POF into the adhesive filled cavity without refraction of the light beam exiting said end and propagating across the adhesive filling the cavity downstream of said end and covering the cross-section thereof.

The coating must also allow easy insertion of the POF into and all along an orifice of an outer tubing (35t). The coating polymers of the present invention have excellent lubricity and can be inserted in close fitting orifices without any trouble.

The refractive index of the coating (33) is not important to the present invention, since the waveguide is formed by the core (31) and cladding (32), whilst the coating (33) acts as a structural stabilizer only.

In one embodiment illustrated in FIGS. 1(d), 6(a), and 6(c), a single cladding (32) is embedded in the coating (33). As discussed supra, the cladding (32) can surround a single or several cores (31). In an alternative embodiment illustrated in FIG. 6(b)&6(d), more than one cladding (32) can be embedded in a single coating (33). Again, each cladding can surround one or more cores (31).

Polymer Optical Fibre (30) (POF)

The polymer optical fibre (POF) (30) of the present invention is composed of a core (31) surrounded by a cladding (32), itself surrounded by a coating (33) as described supra. This POF has been developed for use in AIMD's applications, wherein an optical fibre is implanted in a patient's body to transport light between an encapsulation (50) and a tissue coupling unit (40), as illustrated in FIG. 1(a). The POF of the present invention fulfils all requirements for use in AIMD's applications. First and foremost, all the (co)polymers of the core (31), cladding (32), and coating (33) are available in biocompatible grades off the shelves. This is a mandatory condition before considering any implanted application.

POF's are generally considered as having a low resistance to moisture, which is a major impediment in implantation applications into a very humid environment of a patient's body. Each of the (co)polymers forming the core, cladding, and coating are hydrophobic and are characterized by extremely low water absorption. They are dimensionally and optically very stable in humid environments. These are mandatory conditions for long term implantation applications.

Like most POF's, the POF of the present invention is not brittle contrary to GOF's. This is very important for safety reasons, as breaking an optical fibre in a patient's body is of course to be avoided at all cost. The POF of the present invention is very flexible and can bend to a very small bending radius (R). An optical lead according to the present invention including one or more optical fibres enclosed in an outer tubing, resists without breaking over 47,000 cycles of bending at 90°±5° at a frequency of 2 Hz according to EN 45502-2-1:2014 Active Implantable Medical Devices (Part 2-1).

The mechanical flexibility of the POF of the present invention is combined with a high value of the numerical aperture, NA, of the order of 0.7, and of the corresponding critical angle, θc, of the order of 52 to 53 deg (cf. FIG. 2(d)), which allows maintaining the waveguide function of the POF even when bent at low bending radii (R) (cf. FIG. 2(c)). For example the POF of the present invention can have an optical loss relative to a straight fibre of less than 2% at a bend radius R=2 mm. A high flexibility of the optical fibres coupled to low bending losses is advantageous for use with AIMD's, as

- the optical fibre may require folding and bending during implantation, to accommodate obstacles,
- an angle can be formed between the direction of insertion of the optical fibre to the tissue coupling unit and the direction of the optical fibre extending towards the position of the encapsulation, thus possibly forming acute angles in the optical fibre, and
- patient's movements can bend the optical fibre, and power transmission variations during such movements can only be avoided with optical fibres having low bending losses.

Attenuation losses are in line with most POF's (cf. FIG. 3), and are agreeable in view of the limited length of the POF in an AIMD, generally not exceeding 40 to 50 cm. Coupling losses are minimized due to the high values of NA discussed supra.

The last hurdle for use in AIMD's applications, that the cross-sectional surfaces of the ends of the POF's frayed upon polishing was solved by including a coating (33). By thus mechanically stabilizing the cladding (32) sandwiched between the core (31) and the coating (33), the POF of the present invention can be polished to reach a desired surface smoothness, required for reducing power losses at the level of connectors. The first end and/or the second end of the POF of the present invention is therefore preferably polished, preferably mechanically, chemically, or mechanically-chemically polished. More preferably they are mechanically polished to a desired surface finish.

Optical Lead (35)

In practice, a POF is seldom implanted loose, because it is so thin (outer diameter <530 µm), that it would be very difficult to handle. In general, one or more POF's according to the present invention are enclosed in an outer tubing (35t), as illustrated in FIGS. 1(d), 5(a) & 5(b), and 7.

In case more than one POF is enclosed in the outer tubing, it is preferred to be able to identify each POF at both ends thereof. This is important to ensure that a light source coupled to a first end of one of several POF's is coupled to the corresponding device (PV cell or photodetector) at the second end of the same POF. For example, the POF's can be coloured with a predefined code. This can be achieved by using a coloured coating (33) or, alternatively, a coloured cladding combined with a transparent coating (33). Alternatively, or concomitantly, the outer tubing can be provided with a coloured line or can have a non-revolution cross-section, including e.g., a groove or a protrusion extending along the length thereof, allowing the identification of the required orientation for proper connections of the POF's two ends.

In yet a preferred embodiment, the optical lead (35) is visible to X-rays by including an X-ray visible additive, such as $BaSO_4$, to the outer tubing (35t) or to the coatings (33) of one or more of the polymer optical fibres of the optical lead.

In an embodiment illustrated in FIG. 5(a), the outer tubing can be in the form of a sheath, enclosing one or more POF's, which can be in contact with one another within the sheath. In an alternative embodiment illustrated in FIG. 5(b), the outer tubing can be pultruded, embedding the individual POF's. In a preferred embodiment illustrated in FIG. 5(c), the outer tubing (35t) is a rod comprising a number of elongated parallel orifices extending over the whole length of the rod, having a diameter mating the geometry of the POF's which can be introduced individually in each orifice. In this embodiment, the coating (33) of the POF's must have good lubricity, to allow a smooth insertion of the POF's in the elongated orifices.

The outer tubing (35t) can be made of polymer, preferably of a flexible polymer, such as an elastomer. For example, the tubing can be made of silicone. Of course, like all the other components, the outer tubing material must be biocompatible for medical applications.

FIG. 7 shows different embodiments of optical leads comprising a number of POF's illustrated in FIG. 6.

AIMD

As illustrated in FIG. 1(a), the POF's of the present invention are designed specifically for use with optoelectronic active implantable medical devices (AIMD's) comprising an encapsulation unit (50), a tissue coupling unit (40) comprising electrodes and/or optrodes, and an optical lead (35) comprising one or more POF's (30).

As partially shown in FIG. 1(b), the encapsulation unit (50) is formed by a housing (50h) defining an inner space enclosing one or more optical components including one or more sources of light emission (21L), light sensors, micro-optics components (e.g., lenses), an electronic unit (e.g., an analogue and/or digital circuit) for controlling the one or more sources of light emission and/or for processing any information received from a light sensor, and a source of power for powering the at least one source of light emission and the electronic unit. The source of light emission (21L) emits at least at a wavelength, XI, comprised between 380 and 1800 nm, preferably between 600 and 1500 nm, more preferably between 700 and 900 nm. An example of encapsulation unit suitable for the present invention is described in WO2018068807.

The tissue coupling unit (40) typically can also comprise optical components. If the tissue coupling unit comprises electrodes, they can be activated by transmitting optical energy to a photovoltaic cell located in a connector (40c) of the tissue coupling unit and converting the optical energy into electrical energy and conducting the latter to the electrodes. The optical components can also comprise a photosensor or a source of light emission emitting at least at the wavelength, λI, comprised between 380 and 1800 nm, preferably between 600 and 1500 nm, more preferably between 700 and 900 nm. The source of light emission of the tissue coupling unit can be used, e.g., as a feedback signal. The tissue coupling unit can also be provided with an optrode.

As illustrated in FIG. 1(c), if the tissue to be treated is a nerve, the tissue coupling unit (40) can be in the form of a cuff comprising a support which can be rolled around the nerve to be treated with the electrodes contacting said nerve or with the optrode pointing at said nerve. Examples of cuff electrodes suitable for the present invention are described in PCT/EP2017/081408. Other geometries are adapted for treatments of other tissues, and are well known in the art. The present invention is not restricted to any specific geometry of the tissue coupling unit.

Optical communication between the encapsulation (50) and the tissue coupling unit (40) is ensured by the optical lead (35) comprising one or more POF's according to the present invention. The optical lead (35) has a length of the order of up to 40 or 50 cm and has excellent flexibility, being able to bend with a radius of less than 2 mm without breaking. Optical losses in the POF's themselves can be attributed to attenuation losses, illustrated in FIG. 3, and bending losses (cf. FIG. 2(b), both properties discussed supra and considered as agreeable even at bending radii as low as 2 mm, when POF's according to the present invention are used.

The first and second ends of the optical lead (35) must be connected in optical communication with the optical components of the encapsulation (50) and the tissue coupling unit (40). The connectors (40c, 50c) of the optical lead (35) to the encapsulation (50) and to the tissue coupling unit (40) must therefore be optimized to ensure perfect alignment with the optical components of the encapsulation (50) and the tissue coupling unit (40). Examples of connectors (50c) between an optical lead (35) and an encapsulation (50) are described in PCT/EP2018/073426 and WO2015164571. Examples of connectors (40c) between an optical lead (35) and a tissue coupling unit (40) are described in WO2019042553.

For a given set of connectors (40c, 50c) and optical components, coupling losses are due to the NA of the optical fibres, and the surface finish of the first and second ends of each POF. With POF's according to the present invention, the NA of the order of 0.7 and higher ensures that the coupling losses are limited, and thanks to the stabilization effect of the coating (33) on the cladding (32) and core (31), the POF's ends can be mechanically polished to the desired surface finish to reduce coupling losses due to poor surface finish.

For example, the encapsulation (50) can comprise a source of light emission (21L) and the tissue coupling unit (40) can comprise a photovoltaic cell in conductive communication with electrodes. The optical lead (35) must transport optical energy provided by the source of light emission (21L) to the photovoltaic cell with as little losses as possible. This is made possible with the POF's of the present invention. Further, the tissue coupling unit (40) may be provided with a source of feedback light, coupled to the electrodes and being activated when the electrodes receive electric current. The feedback light emitted by this source of feedback light must be transported to a photosensor located in the encapsulation (50) with as little losses as possible. This too is made possible with the POF's of the present invention.

In this embodiment, it is preferred to use two different POF's, one for coupling the source of light emission (21L) of the encapsulation (50) to the photovoltaic cell of the tissue coupling unit (40), and the other POF for coupling the source of feedback light of the tissue coupling unit to the photosensor of the encapsulation (50). The two (or more) POF's are gathered in an outer tubing (35t) to form an optical lead. As the optical lead can easily be twisted, it is important to couple the first and second ends of each POF at the right position in the connectors (40c, 50c) to avoid optically coupling the photovoltaic cell to the photosensor, which would have no effect at all. Colouring of the POF's as discussed supra helps the artisan to couple the ends of the individual POF's to their corresponding positions in the connectors (40c, 50c).

In a preferred embodiment, the AIMD comprises a cuff electrode unit as illustrated in FIG. 1(c) comprising a photovoltaic cell and comprising, a support sheet (43) which is non-conductive, and having an inner surface and an outer surface separated from the inner surface by a thickness, wherein the support sheet is rolled about a longitudinal axis (Z), forming a cuff of substantially cylindrical geometry such that at least a portion of the inner surface forms an interior of the cuff, and such that at least a portion of the outer surface forms an exterior of the cuff, at least a first connector (40c) including an electrode contact, which is exposed at the inner surface of the cuff and wherein the photovoltaic cell is optically coupled to the second end of the polymer optical fibre and therethrough to the source of light emission (21L) and is electrically coupled to the electrode contact.

For light treatment of a tissue, a so-called optrode can be used. An optrode can be a light emitter focusing a light beam onto a precise area of a tissue, or it can be a light sensor, sensing a reflected, transmitted, or scattered light beam emitted by a light emitter. A light emitter can be in the form of a bevelled edge optical fibre or of an optical fibre coupled to a lens, focusing a light beam on a precise area of a tissue to be treated. Alternatively, the light emitter can be one or more light emitting sources, such as a light emitting diode (LED), a vertical-cavity surface-emitting laser (VCSEL), or another type of laser diode. The light emitting source can be powered by electric current in a similar way to the electrodes discussed supra.

| REF# | Feature |
|---|---|
| 30 | Polymer optical fibre |
| 31 | core |
| 32 | cladding |
| 33 | coating |
| 35 | Optical lead |
| 35t | Outer tubing |
| 40 | Second component = Tissue coupling unit |
| 40c | Connector to the tissue coupling unit |
| 50 | First component = encapsulation |
| 50c | Connector to the encapsulation |

The invention claimed is:

1. A polymer optical fibre (POF) (30) for transmitting light of a wavelength, $\lambda i$, between two separate elements of an active implantable medical device (AIMD), wherein the wavelength, $\lambda i$, is between 380 and 1800 nm and wherein said POF is a multimode optical fibre comprising a first end and a second end, and comprises:
   (a) a core (31) which is cylindrical and made of a cyclic olefin polymer (COP) or copolymer (COC), having a core refractive index n_core at the wavelength, $\lambda i$, the core being enclosed in
   (b) a cladding (32) which has a cladding refractive index n_clad<n_core at the wavelength and which is made of a cladding copolymer comprising monomers of tetrafluoroethylene, hexafluoropropylene and vinylidene fluoride, the cladding being itself enclosed in
   (c) a coating (33) which is made of a coating polymer comprising one of the monomers of the cladding copolymer, and wherein the coating polymer has a higher stiffness than the cladding copolymer,
   wherein the POF has a numerical aperture, NA, at the wavelength, $\lambda i$, of at least 0.5, wherein $NA=((n\_core)^2-(n\_clad)_2)^{1/2}$.

2. The polymer optical fibre according to claim 1, wherein the cladding polymer is a terpolymer of tetrafluoroethylene, hexafluoropropylene and vinylidene fluoride (THV).

3. The polymer optical fibre according to claim 1, wherein the coating polymer is polyvinylidene fluoride (PVDF).

4. The polymer optical fibre according to claim 1, wherein the first end and/or the second end of the polymer optical fibre is polished, preferably mechanically, chemically, or mechanically-chemically polished.

5. The polymer optical fibre according to claim 1, wherein the polymer optical fibre (30) has a diameter (D30) between 150 and 530 μm, and wherein
 a diameter (D31) of the core (31) is between 100 and 300 μm, and/or
 the cladding (32) has a thickness (D32) comprised between 5 and 50 μm, or has an outer diameter (D32) comprised between 130 and 500 μm, and/or
 the coating (33) has a thickness (t33) between 10 and 40 μm.

6. The polymer optical fibre according to claim 1, wherein
 at least two cores are enclosed in a single cladding, or
 at least two claddings enclosing one or more cores, are enclosed in a single coating (33).

7. The polymer optical fibre according to claim 1, wherein the core polymer has an attenuation lower than 4.0 dB/m, at least at one wavelength within the wavelength range from 550 nm to 875 nm.

8. The polymer optical fibre according to claim 1, characterized by an optical loss relative to a straight fibre of less than 2% at a bend radius of 2 mm.

9. An optical lead (35) for transmitting light of wavelength, λi, between two separate elements of an active implantable medical device (AIMD), comprising one or more than one polymer optical fibres (30) according to claim 1 enclosed in an outer tubing (35t).

10. The optical lead according to claim 9, wherein at least one polymer optical fibre is coloured.

11. The optical lead according to claim 9, which is visible to X-rays by including an X-ray visible additive to the outer tubing (35t) or to the coatings (33) of one or more of the polymer optical fibres of the optical lead.

12. An active implantable medical device (AIMD) comprising:
 (a) an encapsulation comprising a source of light emitting at least at a wavelength, λi, comprised between 380 and 1800 nm,
 (b) a tissue coupling unit, separate from the encapsulation and comprising a photovoltaic cell and/or a photosensor, and/or an optrode,
 (c) the source of light of the encapsulation being optically coupled to the first end of a polymer optical fibre and the photovoltaic cell and/or photosensor and/or optrode of the tissue coupling unit, and being optically coupled to the second end of the polymer optical fibre, such that the source of light is in optical communication with the photovoltaic cell and/or photosensor and/or optrode through the polymer optical fibre;
 wherein the polymer optical fibre is according to claim 1.

13. The active implantable medical device according to claim 12, comprising more than one polymer optical fibres gathered in an outer tubing (35t) to form an optical lead enclosed in an outer tubing (35t).

14. The active implantable medical device according to claim 12, wherein the tissue coupling unit is a cuff electrode unit comprising a photovoltaic cell, and comprising:
 a support sheet (43) which is non-conductive, and has an inner surface and an outer surface separated from the inner surface by a thickness, wherein the support sheet is rolled about a longitudinal axis (Z), forming a cuff of substantially cylindrical geometry such that at least a portion of the inner surface forms an interior of the cuff, and such that at least a portion of the outer surface forms an exterior of the cuff,
 at least a first connector (40c) including an electrode contact, which is exposed at the inner surface of the cuff and wherein
 the photovoltaic cell is optically coupled to the second end of the polymer optical fibre and therethrough to the source of light emission (21L) and is electrically coupled to the electrode contact.

15. The polymer optical fibre according to claim 1 wherein the wavelength, λi, is between 650 and 1550 nm.

16. The polymer optical fibre according to claim 1 wherein the NA is at least 0.6.

17. The optical lead according to claim 10, wherein at least one polymer optical fibre comprises a coloured coating or a coloured cladding combined with a transparent coating.

18. The optical lead according to claim 10, which is visible to X-rays by including an X-ray visible additive to the outer tubing (35t) or to the coatings (33) of one or more of the polymer optical fibres of the optical lead.

19. The active implantable medical device according to claim 13, wherein the tissue coupling unit is a cuff electrode unit comprising a photovoltaic cell, and comprising:
 a support sheet (43) which is non-conductive, and has an inner surface and an outer surface separated from the inner surface by a thickness, wherein the support sheet is rolled about a longitudinal axis (Z), forming a cuff of substantially cylindrical geometry such that at least a portion of the inner surface forms an interior of the cuff, and such that at least a portion of the outer surface forms an exterior of the cuff,
 at least a first connector (40c) including an electrode contact, which is exposed at the inner surface of the cuff and wherein
 the photovoltaic cell is optically coupled to the second end of the polymer optical fibre and therethrough to the source of light emission (21L) and is electrically coupled to the electrode contact.

\* \* \* \* \*